United States Patent [19]

Suzuki et al.

[11] Patent Number: 5,003,977
[45] Date of Patent: Apr. 2, 1991

[54] DEVICE FOR ANALYZING FLUORESCENT LIGHT SIGNALS

[75] Inventors: Susumu Suzuki; Kazuyuki Ishida, both of Hamamatsu; Takeo Ozaki, Hamakita, all of Japan

[73] Assignees: Agency of Industrial Science & Technology; Ministry of International Trade & Industry, both of Tokyo, Japan

[21] Appl. No.: 321,296

[22] Filed: Mar. 9, 1989

[51] Int. Cl.$^5$ .......................... A61B 1/06; A61B 6/00
[52] U.S. Cl. .................... 128/633; 128/634; 128/665; 606/10
[58] Field of Search ............... 128/633, 634, 664, 665, 128/395; 606/15, 16, 7, 10

[56] References Cited

U.S. PATENT DOCUMENTS

| | | | |
|---|---|---|---|
| 4,576,173 | 3/1986 | Parker | 128/634 |
| 4,768,513 | 9/1988 | Suzuki | 128/665 |
| 4,852,579 | 8/1989 | Gilstad | 128/665 |

*Primary Examiner*—Lee S. Cohen
*Assistant Examiner*—John C. Hanley
*Attorney, Agent, or Firm*—Oblon, Spivak, McClelland, Maier & Neustadt

[57] ABSTRACT

A device for analyzing fluorescent light signals consists of memory means for storing as a reference spectrum a spectrum obtained under predetermined conditions, and extraction means for extracting a predetermined component spectrum based on the results of a conversion of the reference spectrum using a specific wavelength of a measured spectrum obtained during actual measurement and a specific wavelength of the reference spectrum. The arrangement of the invention allows the spectrum of a specific component to be extracted accurately from measured spectra.

3 Claims, 3 Drawing Sheets

DEVICE FOR ANALYZING FLUORESCENT LIGHT SIGNALS

BACKGROUND OF THE INVENTION

1. Field of the Invention

This invention relates to a device for analyzing fluorescent light signals in which organisms previously injected with a hematoporphyrin derivative (hereinafter abbreviated as HPD) or other fluorescent substances which have a strong affinity for tumors are irradiated with laser light at predetermined positions such as the trachea, bladder, etc. in order to produce fluorescent light, and tumors in them are diagnosed by means of the intensity of the fluorescence produced at this time.

2. Prior Art Statement

Methods and devices for cancer diagnosis and therapy utilizing the photochemical reactions between laser light and fluorescent substances such as HPD which have a strong affinity for tumors have been proposed (Japanese Patent Application Disclosures Nos. SHO 59-40830 and SHO 59-40869, U.S. Pat. No. 4,556,057).

FIG. 3 is a block drawing illustrating the basic configuration of a diagnostic device of the prior art. The device of FIG. 3 is provided with an ordinary endoscopic diagnostic system 50, a photochemical reaction diagnostic/therapeutic system 51, and a fiber bunch 52. The fiber bunch 52 consists of an image guide 53 and light guides 54, 55 and 56. One end of the fiber bunch 52 is inserted into the patient's body at a position 70 suspected to be the focus, the patient having been previously given an intravenous injection of HPD, and the other end is connected to the endoscopic diagnostic system 50 and the photochemical reaction diagnostic/therapeutic system 51.

The endoscopic diagnostic system 50 consists of a white light source 57 for illuminating the tissue surface at the position 70, the light guide 54 for conducting this light, the image guide 53 for conducting images of the tissue surface to the color camera 58, and a monitor 59 for displaying images of the tissue surface picked up by the color camera 58.

The photochemical reaction diagnostic/therapeutic system 51 is equipped with a laser light source 60, a high-sensitivity camera 62, an analytical circuit 63 and a monitor 64. The laser light source 60 outputs both exciting laser light for diagnosis (405 nm) and laser light for therapy (630 nm), which is irradiated onto the position 70 by means of the light guide 55.

The fluorescence produced by the exciting light from the laser light source 60 irradiated onto the position 70 is conducted by the light guide 56 to a spectroscope 61.

Fluorescence spectrum images SP obtained from the spectroscope 61 are picked up by the high-sensitivity camera 62 which outputs video signals SVO that are arithmetically processed in the analytical circuit 63, and the images are displayed on the monitor 64 as spectrum patterns. The spectrum images SP are set within a wavelength region of 600 to 700 nm so that it will be possible to observe the spectrum with two peaks at 630 nm and 690 nm which is a characteristic of HPD fluorescence.

Since in this type of system endoscopic diagnosis and photochemical reaction diagnosis/therapy are carried out concurrently, the white light source 57 and laser light source 60 are driven to irradiate alternately, using a timesharing system. The fluorescence spectrum system from the spectroscope 61 to the monitor 64 is operated intermittently, in synchronization with the irradiation of laser light from the laser light source 60.

Using this device, during diagnosis the operator can locate the position of a cancer while viewing at the same time the tissue images on the monitor 59 and the fluorescence spectrum patterns on the monitor 64. If a cancer is discovered, the operator can perform therapy immediately by merely switching over the light from exciting light to therapeutic light. Therapy is carried out by means of a photochemical reaction between the HPD remaining in the cancerous part and the therapeutic light. This causes necrosis selectively at the cancerous part only.

Furthermore, as for the confirmation of fluorescence during diagnosis, the spectrum patterns which are unique to the fluorescence themselves are observed directly, making it possible to determine the presence of cancer easily. This can contribute greatly to the early diagnosis and therapy of cancer.

As was described above, this device utilizes the affinity of HPD for tumors in diagnosis and therapy. For diagnosis in particular, it is configured so that it detects the fluorescence spectrum from HPD.

However, as when the tissue surface is irradiated with exciting light in the 405 nm wavelength region spontaneous fluorescence is also emitted from normal tissue, the spectrum that is actually picked up consists of HPD fluorescence on which is superimposed spontaneous fluorescence in the form of background noise. This is reported in, for example, "Laser in Surgery and Medicine," 4, 49–58 (1984).

FIG. 4 shows an example of the total fluorescence spectrum intensity $I_{TOT}$, the spontaneous fluorescence spectrum intensity $I_{AUTO}$, and HPD fluorescence spectrum intensity $I_{HPD}$. As can be seen from FIG. 4, total fluorescence spectrum intensity $I_{TOT}$ has HPD fluorescence spectrum intensity $I_{HPD}$ and spontaneous fluorescence spectrum intensity $I_{AUTO}$ superimposed thereon. For purposes of diagnosis this is not a problem if the spontaneous fluorescence spectrum intensity $I_{AUTO}$ is sufficiently smaller than HPD fluorescence spectrum intensity $I_{HPD}$. In most cases, however, spontaneous fluorescence spectrum intensity $I_{AUTO}$ is usually about the same as HPD fluorescence spectrum intensity $I_{HPD}$ or greater. Also, spontaneous fluorescence spectrum intensity $I_{AUTO}$ and HPD fluorescence spectrum intensity $I_{HPD}$ are subjected to complex and extensive changes by the areal ratio of normal tissue parts to abnormal tissue parts (cancer parts) in the field of observation, the relative distance between light guides 55 and 56 and the tissue surface, and the laser irradiation angle and detection angle relative to the tissue surface. Because of this, in actual diagnosis, it has been very difficult to accurately detect the HPD fluorescence spectrum intensity $I_{HPD}$.

SUMMARY OF THE INVENTION:

The object of the present invention is to provide a device for analyzing fluorescent light signals which enables a specific component spectrum, such as an HPD fluorescence spectrum, to be extracted accurately.

In order to achieve the aforesaid object, the device for analyzing fluorescent light signals according to the present invention is provided with memory means for storing as a reference spectrum a spectrum obtained under predetermined conditions; extraction means for extracting a predetermined component spectrum based on the results of a conversion of the reference spectrum using specific wavelengths of a measured spectrum obtained during actual measurement and specific wavelengths of the reference spectrum. Preferably, a wavelength selected for the above specific wavelength should be one at which the predetermined component spectrum extracted by the extraction means is zero.

A spectrum obtained under predetermined conditions, for example a measured spontaneous fluorescence spectrum just from normal parts, is stored in the memory means as reference spectrum $S_o(\lambda_i)$. A spectrum $S_{in}(\lambda_i)$, such as, for example, a fluorescence spectrum, from a predetermined part is then measured; here, the $S_{in}(\lambda_i)$ will consist of the predetermined component spectrum, such as the HPD component spectrum, on which is superimposed other component spectra, such as for example a spontaneous fluorescence spectrum.

However, between the time when reference spectrum $S_o(\lambda_i)$ is measured and the time when spectrum $S_{in}(\lambda_i)$ is measured there is generally a variation such as in the measurement environment, tissues, and the like, so that even if the reference spectrum $S_o(\lambda_i)$ is subtracted from the spectrum $S_{in}(\lambda_i)$, the predetermined component spectrum cannot be accurately extracted. This being the case, in accordance with the present invention, a specific wavelength $\lambda_o$ of the spectrum $S_{in}(\lambda_i)$ is employed as $S_{in}(\lambda_o)$ to convert spectrum $S_o(\lambda_i)$, (for example, by $S_{in}(\lambda_o) \cdot S_o(\lambda_i)/S_o(\lambda_o)$), and on the basis of this conversion the predetermined component spectrum is extracted from the measured spectrum. Thus, in the measurement, variations in the measurement environment, tissues, etc. are followed to enable the predetermined component spectrum to be extracted accurately.

Other purposes and characteristics of this invention will be clarified in the ensuing detailed explanation on the basis of the attached drawings.

DESCRIPTION OF THE PREFERRED EMBODIMENT

Figure 1:
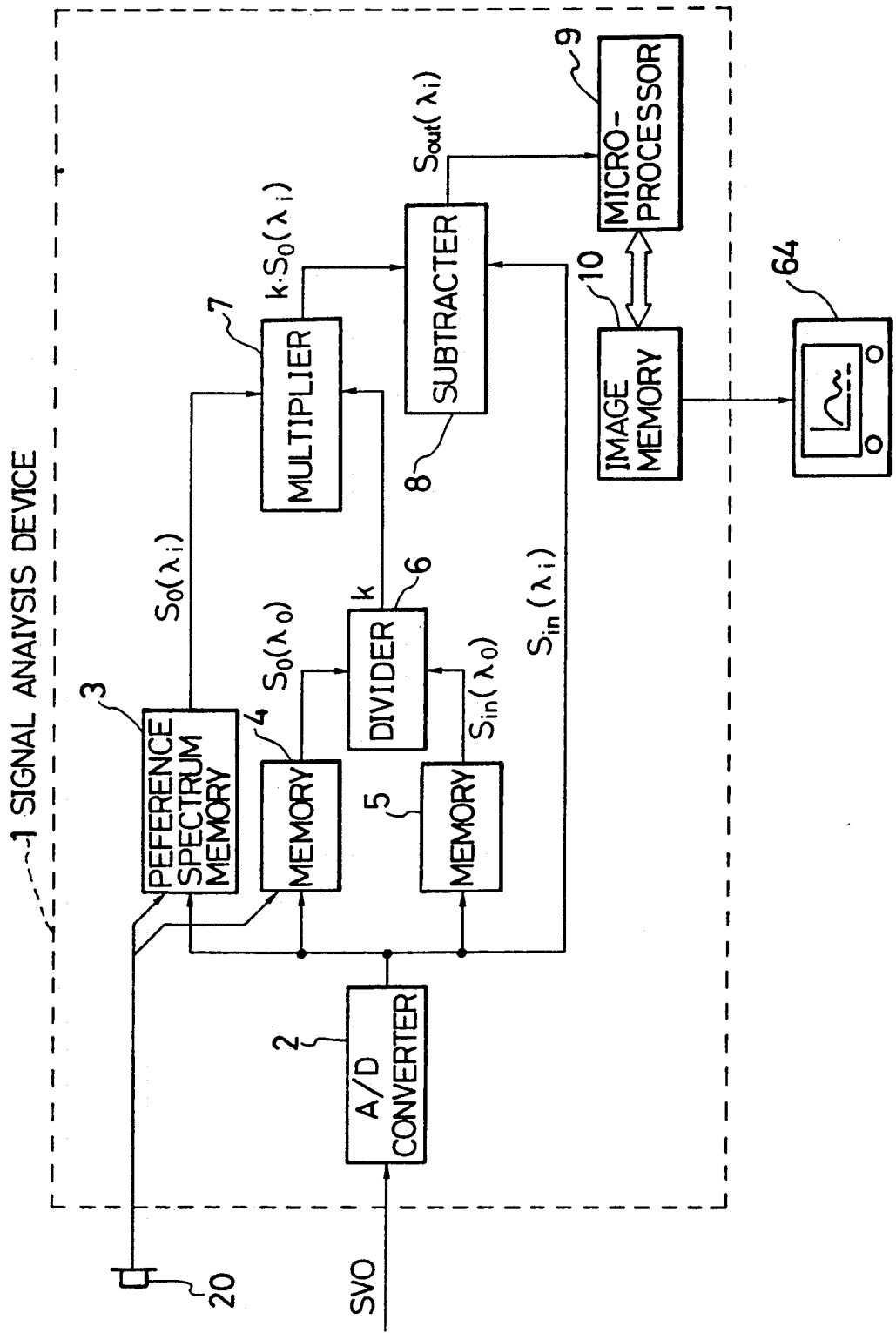
FIG. 1 is a block drawing illustrating an embodiment of a device for analyzing fluorescent light signals according to the present invention.

FIG. 1 is a block drawing of an embodiment of a device for analyzing signals according to the present invention. With reference to FIG. 1, a signal analysis device 1 of this embodiment is equipped with an A/D converter 2; a reference spectrum memory 3 and memory 4 that form memory means for storing the reference spectrum; a memory 5, divider 6, multiplier 7 and subtracter 8 forming the extraction means for extracting the HPD fluorescence spectrum from the fluorescence spectrum; a microprocessor 9; and an image memory 10.

Figure 2:
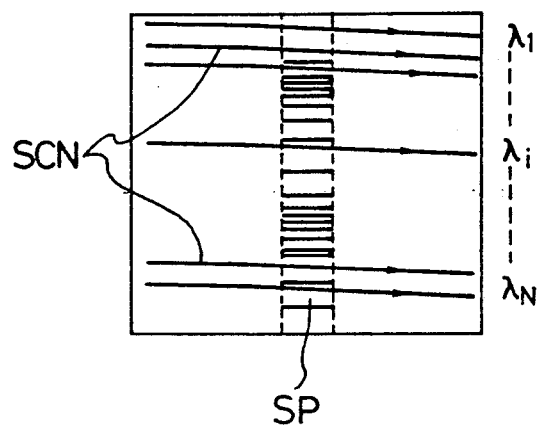
FIG. 2 is an explanatory view illustrating the method of obtaining spectrum video signals.

Spectrum video signals SVO are input into the signal analysis device 1. Spectrum video signals SVO are video signals output when fluorescence spectrum images SP divided by a spectroscope or the like are scanned by scanning lines SCN, as shown in FIG. 2, using a means such as a high sensitivity camera.

In the fluorescence spectrum image SP the wavelength increases going from top to bottom, therefore the spectrum video signals SVO can be sampled for each wavelength $\lambda_i (1 \leq i \leq N)$ in the order of the scanning lines SCN. If for example a wavelength $\lambda_1$ corresponding to the first scanning line is set at 580 nm and a wavelength $\lambda_N$ corresponding to the final scanning line is set at 720 nm, spectrum video signals SVO are sampled from 580 nm to 720 nm on a time series basis. Also, the amplitude of the spectrum video signals SVO at the scanning lines SCN corresponds to the spectral intensity at the corresponding wavelength $\lambda_i$.

Moreover, the spectrum video signals SVO mirror the spontaneous fluorescence spectrum when fluorescence from normal tissue parts is picked up. Also, when during actual diagnosis abnormal tissue parts are included, the fluorescence spectrum consists of a spontaneous fluorescence spectrum superimposed on an HPD fluorescence spectrum.

The A/D converter 2 performs an analog to digital conversion on the spectrum video signals SVO and outputs the result to the memory means and extraction means described above.

When spontaneous fluorescence from normal tissue parts is detected, the spontaneous fluorescence spectrum of each wavelength $\lambda_i$ is stored in the reference spectrum memory 3 as reference spectrum $S_o(\lambda_i)$, while the reference spectrum $S_o(\lambda_o)$ of a specific wavelength $\lambda_o$ is stored in memory 4.

During actual diagnosis the fluorescence spectrum $S_{in}(\lambda_o)$ of a specific wavelength $\lambda_o$ is stored in memory 5. The divider 6 obtains the ratio of the spectra $S_o(\lambda_o)$ and $S_{in}(\lambda_o)$ stored in memories 4 and 5 as a constant k ($= S_{in}(\lambda_o)/S_o(\lambda_o)$). With the multiplier 7 and subtracter 8, a reference spectrum $S_o(\lambda_i)$ that is of the same wavelength as the wavelength $\lambda_i$ of the fluorescence spectrum $S_{in}(\lambda_i)$ during actual diagnosis is multiplied by the constant k, the result of the multiplication $k \cdot S_o(\lambda_i)$ is subtracted from the fluorescence spectrum $S_{in}(\lambda_i)$ and the result of the subtraction $S_{OUT}(= S_{in}(\lambda_i) - k \cdot S_o(\lambda_i))$ is output as the HPD fluorescence spectrum.

Differentiating between the reference spectrum $S_o(\lambda_i)$ and the fluorescence spectrum $S_{in}(\lambda_i)$ according to the tissue parts that are measured (reference spectrum $S_o(\lambda_i)$) being the measured spectrum of normal tissue parts and fluorescence spectrum $S_{in}(\lambda_i)$ being the measured spectrum of the part to be measured), because in the measurement process there is generally variation in the measurement environment (for example, in the angles and relative distance between the light guides 55 and 56 and the tissue surface), and with the measurement times also being different, there may be movement of the tissue in the intervening time, and there is a relative discrepancy between the amounts of light detected, it is not possible to regard the spontaneous fluorescence spectrum superimposed on the fluorescence spectrum $S_{in}(\lambda_i)$ as being of the same size as the reference spectrum $S_o(\lambda_i)$ stored in the reference spectrum memory 3. Therefore, the spontaneous fluorescence spectrum superimposed on the fluorescence spectrum $S_{in}(\lambda_i)$ cannot be accurately removed even if the reference spectrum $S_o(\lambda_i)$ is subtracted directly from the fluorescence spectrum $S_{in}(\lambda_i)$.

Figure 4:
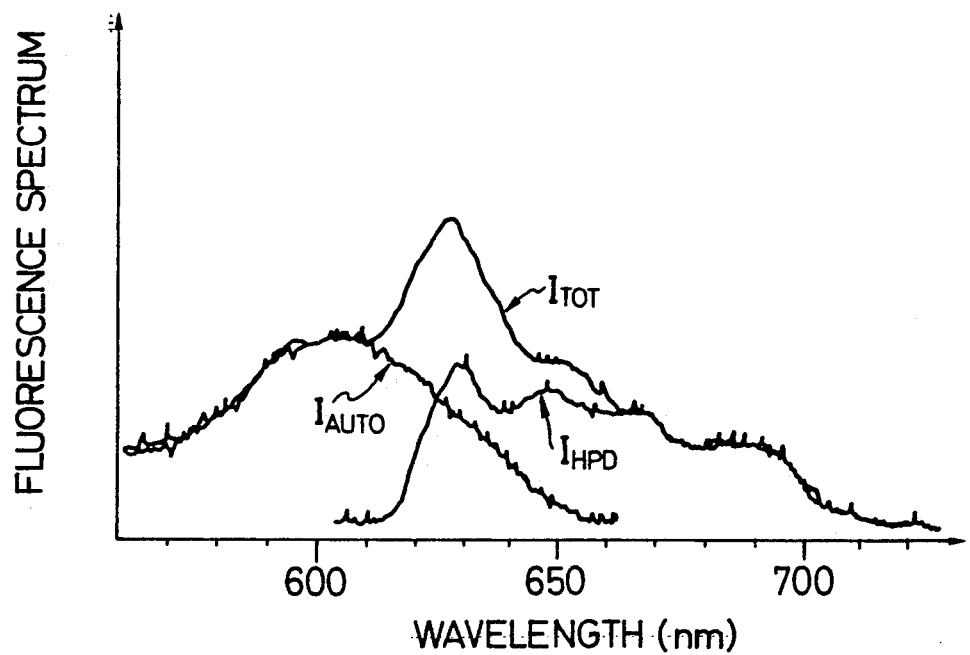
FIG. 4 is graph illustrating a fluorescence spectrum.
Figure 3:
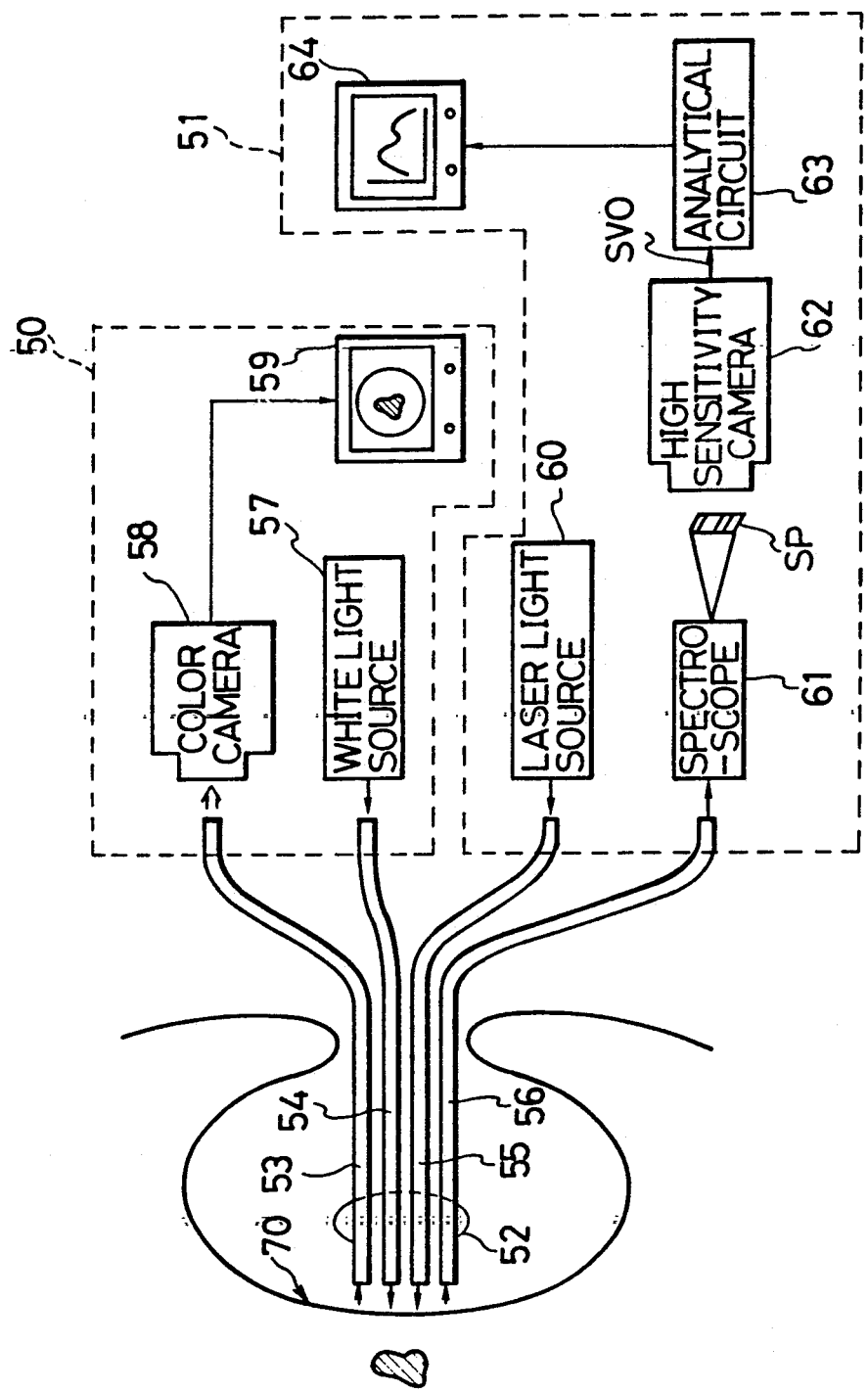
FIG. 3 is a block diagram illustrating a known cancer diagnosis and therapy device utilizing photochemical reaction.

The constant k is for converting differences in the size of the reference spectrum $S_o(\lambda_i)$ caused by variation in the measurement environment and the tissue, etc., and the size of the spontaneous fluorescence spectrum superimposed on the fluorescence spectrum $S_{in}(\lambda_i)$. As the specific wavelength $\lambda_o$ for determining the constant k, a wavelength is chosen at which the intensity of the HPD fluorescence spectrum is close to zero and the intensity of the spontaneous fluorescence spectrum is relatively large. In the example shown in FIG. 4, a wavelength $\lambda_o$ of 600 nm, for example, is appropriate. That is, at this wavelength $\lambda_o$ virtually the whole of the fluorescence spectrum $S_{in}(\lambda_o)$ will be composed of spontaneous fluorescence and $k \cdot S_o(\lambda_i)$ will be close to the spontaneous fluorescence spectrum superimposed on the fluorescence spectrum $S_{in}(\lambda_i)$.

The operation of the signal analysis device 1 configured as described above will now be described. First, in order to sample spontaneous fluorescence spectra from normal tissue parts, that is, reference spectrum $S_o(\lambda_i)$, the operator aligns the endoscopic field of view with the normal tissue and irradiates it with light from the laser light source 60, and while visually confirming the alignment on the monitor 64 pushes a spectral sampling switch 20. In accordance with this timing, the spectrum video signals SVO, that is, the reference spectrum $S_o(\lambda_i)$, which have been converted to digital signals are sequentially stored in the reference spectrum memory 3. At the same time the value $S_o(\lambda_o)$ at reference spectrum $S_o(\lambda_i)$ wavelength $\lambda_o$ (for example, 600 nm) is stored in the memory 4.

Next, in the diagnosis procedure the operator aligns the endoscopic field of view with the tissue to be measured and irradiates it with light from the laser light source 60. This causes the fluorescence spectrum $S_{in}(\lambda_i)$ to be output from the A/D converter 2 in the order of the wavelengths $\lambda_i$. The value of $S_{in}(\lambda_o)$ at fluorescence spectrum $S_{in}(\lambda_i)$ wavelength $\lambda_o$ (600 nm, for example) is written into the memory 5, at which point the divider 6 outputs a constant k $(=S_{in}(\lambda_o)/S_o(\lambda_o))$. A reference spectrum $S_o(\lambda_i)$ of wavelength $\lambda_i$ that is the same as the fluorescence spectrum $\lambda_i$ just input is read out from the reference spectrum memory 3, the result of the multiplication $k \cdot S_o(\lambda_i)$ is output by the multiplier 7 and the result of the subtraction $S_{OUT}\lambda_i(=S_{in}(\lambda_i)-K \cdot S_o(\lambda_i))$ is output by the subtracter. The subtraction result $S_{OUT}\lambda_i$ is the result of the subtraction of the spontaneous fluorescence spectrum under the condition "$S_{OUT}\lambda_o = 0$." The subtraction result $S_{OUT}\lambda_i$ is displayed graphically on the monitor 64 by the microprocessor 9 via the image memory 10. By this means, the processing for the removal of the spontaneous fluorescence spectrum from the fluorescence spectrum can follow variation in the detected light amount caused by movement of measurement environment, tissue, etc., enabling the HPD fluorescence spectrum needed for diagnosis to be extracted accurately.

As has been explained, if the present invention is adapted to a cancer diagnostic device in accordance with which specific wavelengths of a spectrum obtained by actual measurement and specific wavelengths of a reference spectrum are used to convert the reference spectrum, and based on the conversion result a predetermined component spectrum can be extracted from the measured spectrum, so that by using exciting light to irradiate a part injected beforehand with a fluorescent substance such as, for example, HPD, thereby causing it to emit fluorescent light for cancer diagnosis using the HPD fluorescence spectrum that is produced thereby, the spontaneous fluorescence spectrum superimposed on the HPD fluorescence spectrum can be effectively removed to thereby enable the HPD required for diagnosis to be extracted accurately.

What is claimed is:

1. A device for analyzing fluorescent light signals, comprising:
   first light-irradiating means for irradiating a normal position of an organism with first laser light;
   first light-detecting means for detecting a first spectrum of fluorescence excited by the irradiation of said first laser light;
   memory means for storing, as a reference spectrum, the first spectrum of fluorescence detected by said first light-detecting means;
   second light-irradiating means for irradiating with second laser light a position to be diagnosed of the organism injected with a fluorescent substance having a strong affinity for tumors;
   second light-detecting means for detecting a second spectrum of fluorescence excited by the irradiation of said second laser light;
   correction means for correcting said reference spectrum on the basis of a ratio of an intensity of a specific wavelength in the second spectrum detected by said second light-detecting means to an intensity of the same wavelength as said specific wavelength in said reference spectrum; and
   extraction means for subtracting the corrected reference spectrum from the detected second spectrum and extracting the difference.

2. A device for analyzing fluorescent light signals, comprising:
   light-irradiating means for irradiating with a laser a normal position of an organism and a position to be diagnosed of said organism injected with a fluorescent substance having a strong affinity for tumors;
   light-detecting means for detecting a first spectrum of fluorescence excited by irradiation of said normal position by said light-irradiating means and a second spectrum of fluorescence excited by irradiation of said diagnosed position by said light-irradiating means;
   first memory means for storing said first spectrum, said first spectrum being used as a reference spectrum;
   second memory means for storing an intensity at a wavelength in said first spectrum and for storing an intensity of said wavelength in said second spectrum;
   correction means for correcting said reference spectrum by multiplying said reference spectrum by a ratio of said intensity at said wavelength in said first spectrum to said intensity at said second wavelength in said spectrum; and
   extraction means for subtracting said corrected reference spectrum from said second spectrum and for outputting the difference.

3. A device as recited in claim 2, wherein:
   said first spectrum at said wavelength has a much greater intensity than said second spectrum at said wavelength.

* * * * *

UNITED STATES PATENT AND TRADEMARK OFFICE
CERTIFICATE OF CORRECTION

PATENT NO. : 5,003,977
DATED : April 2, 1991
INVENTOR(S) : Susumu Suzuki et al.

It is certified that error appears in the above-identified patent and that said Letters Patent is hereby corrected as shown below:

On the title page:
   The Foreign Application Priority Data has been omitted, should be, --Mar. 31, 1988 [JP]   Japan...........63-75858--, and the Assignee is incorrect, should be, --Agency of Industrial Science & Technology, Ministry of International Trade & Industry, Tokyo, Japan--.

Signed and Sealed this

Sixth Day of October, 1992

Attest:

DOUGLAS B. COMER

Attesting Officer          Acting Commissioner of Patents and Trademarks